(12) United States Patent
Nakagawa

(10) Patent No.: US 11,445,898 B2
(45) Date of Patent: Sep. 20, 2022

(54) OPTICAL MODULE FOR ENDOSCOPE, ENDOSCOPE, AND MANUFACTURING METHOD FOR OPTICAL MODULE FOR ENDOSCOPE

(71) Applicant: OLYMPUS CORPORATION, Tokyo (JP)

(72) Inventor: Yusuke Nakagawa, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 917 days.

(21) Appl. No.: 16/251,597

(22) Filed: Jan. 18, 2019

(65) Prior Publication Data

US 2019/0167084 A1 Jun. 6, 2019

Related U.S. Application Data

(63) Continuation of application No. PCT/JP2016/074956, filed on Aug. 26, 2016.

(51) Int. Cl.
*A61B 1/00* (2006.01)
*A61B 1/05* (2006.01)
(Continued)

(52) U.S. Cl.
CPC ............ *A61B 1/051* (2013.01); *A61B 1/0011* (2013.01); *A61B 1/00013* (2013.01);
(Continued)

(58) Field of Classification Search
None
See application file for complete search history.

(56) References Cited

U.S. PATENT DOCUMENTS

| 7,004,644 B1 | 2/2006 | Johnson |
| 2008/0013959 A1 | 1/2008 | Ishigami |

(Continued)

FOREIGN PATENT DOCUMENTS

| EP | 2 624 304 A1 | 8/2013 |
| EP | 3 075 298 A1 | 10/2016 |

(Continued)

OTHER PUBLICATIONS

International Search Report dated Nov. 1, 2016 received in PCT/JP2016/074956.

*Primary Examiner* — Timothy J Neal
(74) *Attorney, Agent, or Firm* — Scully, Scott, Murphy & Presser, P.C.

(57) ABSTRACT

An optical module for endoscope includes an optical fiber, an optical element, a first substrate including, on a first principal plane, an insertion hole into which the optical fiber is inserted, the optical element being mounted on a second principal plane of the first substrate, a second substrate, on a third principal plane of which a recessed section in which the optical element is housed is present, and a solder ring that bonds a seal ring of the second principal plane of the first substrate and a guard ring of the third principal plane of the second substrate. The first substrate and the second substrate have the same external dimension in an optical axis orthogonal direction, and side surfaces of the first substrate and the second substrate are present in the same plane.

17 Claims, 16 Drawing Sheets

(51) Int. Cl.
   *G02B 6/42*    (2006.01)
   *G02B 23/26*   (2006.01)
   *G02B 23/24*   (2006.01)

(52) U.S. Cl.
   CPC ...... *A61B 1/00096* (2013.01); *A61B 1/00167* (2013.01); *G02B 6/42* (2013.01); *G02B 6/423* (2013.01); *G02B 6/424* (2013.01); *G02B 6/428* (2013.01); *G02B 6/4259* (2013.01); *G02B 23/26* (2013.01); *G02B 6/4214* (2013.01); *G02B 23/2469* (2013.01)

(56) References Cited

U.S. PATENT DOCUMENTS

| | | |
|---|---|---|
| 2012/0193742 A1 | 8/2012 | Hirano et al. |
| 2012/0195545 A1 | 8/2012 | Yasuda et al. |
| 2013/0182099 A1 | 7/2013 | Nakamura |
| 2015/0342530 A1 * | 12/2015 | Dekker .................. A61B 1/051 600/478 |
| 2016/0262599 A1 | 9/2016 | Nakagawa |

FOREIGN PATENT DOCUMENTS

| | | |
|---|---|---|
| JP | 2003-503858 A | 1/2003 |
| JP | 2005-292739 A | 10/2005 |
| JP | 2005-353637 A | 12/2005 |
| JP | 2007-324303 A | 12/2007 |
| JP | 2007324303 A * | 12/2007 |
| JP | 2008-20620 A | 1/2008 |
| JP | 2012-79851 A | 4/2012 |
| JP | 2012-160526 A | 8/2012 |
| JP | 2012-160527 A | 8/2012 |
| JP | 2013-110164 A | 6/2013 |
| JP | 2013-168509 A | 8/2013 |
| JP | 2015-68835 A | 4/2015 |
| JP | 2015-104387 A | 6/2015 |
| JP | 2015-524285 A | 8/2015 |
| WO | 01/01497 A1 | 1/2001 |
| WO | 2012/043187 A1 | 4/2012 |
| WO | 2014/006536 A2 | 1/2014 |
| WO | 2015/079780 A1 | 6/2015 |

* cited by examiner

OPTICAL MODULE FOR ENDOSCOPE, ENDOSCOPE, AND MANUFACTURING METHOD FOR OPTICAL MODULE FOR ENDOSCOPE

CROSS REFERENCE TO RELATED APPLICATION

This application is a continuation application of PCT/JP2016/074956 filed on Aug. 26, 2016, the entire contents of which are incorporated herein by this reference.

BACKGROUND OF THE INVENTION

Field of the Invention

The present invention relates to an optical module for endoscope including an optical fiber, a first substrate on which an optical element is mounted, a second substrate including a recessed section in which the optical element is housed, and a solder ring that bonds the first substrate and the second substrate, an endoscope including the optical module for endoscope, and a manufacturing method for an optical module for endoscope including an optical fiber, a first substrate on which an optical element is mounted, a second substrate including a recessed section in which the optical element is housed, and a solder ring that bonds the first substrate and the second substrate.

Description of the Related Art

An endoscope includes an image pickup apparatus including an image pickup device such as a CCD at a distal end portion of an elongated insertion section. In recent years, use of an image pickup device including a large number of pixels in an endoscope has been examined. In an image pickup apparatus in which the image pickup device including a large number of pixels is used, an amount of signals transmitted from the image pickup device to a signal processing apparatus increases. Therefore, optical signal transmission via an optical fiber by an optical signal is desirable instead of electric signal transmission via a metal wire by an electric signal. For the optical signal transmission, an E/O optical module (an electrooptical converter) that converts an electric signal into an optical signal and an O/E optical module (a photoelectric converter) that converts an optical signal into an electric signal are used.

Reduction in size of an optical module is important for reduction in a diameter of an endoscope. An optical element is desirably hermetically sealed for improvement of reliability of the optical module. Note that a method of manufacturing a plurality of optical modules on a wafer level and cutting and singulating the plurality of optical modules in order to efficiently produce small optical modules is known.

Japanese Patent Application Laid-Open Publication No. 2007-324303 discloses a manufacturing method for a wafer-level optical module. The optical module is manufactured by bonding, via annular solder, a transparent substrate mounted with an optical element to a package including a recessed section in which the optical element is housed.

SUMMARY OF THE INVENTION

An optical module for endoscope in an embodiment includes: an optical fiber configured to transmit an optical signal; an optical element including a light emitting section configured to output the optical signal or a light receiving section to which the optical signal is inputted and an external terminal connected to the light emitting section or the light receiving section; a first substrate including a first principal plane and a second principal plane opposed to the first principal plane, an insertion hole into which the optical fiber is inserted being present on the first principal plane and the optical element being mounted on the second principal plane; a second substrate including a third principal plane and a fourth principal plane opposed to the third principal plane, a recessed section in which the optical element is housed being present on the third principal plane; and a solder ring configured to bond an annular seal ring of the second principal plane of the first substrate and an annular guard ring of the third principal plane of the second substrate and seal up the recessed section. The first substrate includes, on the second principal plane, a connection electrode disposed on an inner side of the seal ring and electrically connecting the external terminal of the optical element and the seal ring bonded together. The second substrate includes a lower electrode on the fourth principal plane and further includes a through-wire electrically connecting the guard ring of the third principal plane and the lower electrode. The external terminal of the optical element is electrically connected to the lower electrode via the connection electrode, the seal ring, the solder ring, the guard ring, and the through-wire.

An optical module for endoscope in another embodiment includes: an optical fiber configured to transmit an optical signal; an optical element including a light emitting section configured to output the optical signal or a light receiving section to which the optical signal is inputted and an external terminal connected to the light emitting section or the light receiving section; a first substrate including a first principal plane and a second principal plane opposed to the first principal plane, the optical element being mounted on the second principal plane; a second substrate including a third principal plane and a fourth principal plane opposed to the third principal plane, the optical element being housed in a recessed section of the third principal plane; and a solder ring configured to bond the first substrate and the second substrate. An annular seal ring of the second principal plane of the first substrate and a guard ring of the third principal plane of the second substrate are bonded via the solder ring. The recessed section is sealed up. The first substrate includes, on the second principal plane, a connection electrode disposed on an inner side of the seal ring and electrically connecting the external terminal of the optical element and the seal ring bonded together. The second substrate includes a lower electrode on the fourth principal plane and further includes a through-wire electrically connecting the guard ring of the third principal plane and the lower electrode. The external terminal of the optical element is electrically connected to the lower electrode via the connection electrode, the seal ring, the solder ring, the guard ring, and the through-wire.

An endoscope in another embodiment includes an optical module for endoscope. The optical module for endoscope includes: an optical fiber configured to transmit an optical signal; an optical element including a light emitting section configured to output the optical signal or a light receiving section to which the optical signal is inputted and an external terminal connected to the light emitting section or the light receiving section; a first substrate including a first principal plane and a second principal plane opposed to the first principal plane, an insertion hole into which the optical fiber is inserted being present on the first principal plane and the optical element being mounted on the second principal plane; a second substrate including a third principal plane and a fourth principal plane opposed to the third principal plane, a recessed section in which the optical element is housed being present on the third principal plane; and a solder ring configured to bond an annular seal ring of the second principal plane of the first substrate and an annular guard ring of the third principal plane of the second substrate and seal up the recessed section. The first substrate includes, on the second principal plane, a connection electrode disposed on an inner side of the seal ring and electrically connecting the external terminal of the optical element and the seal ring bonded together. The second substrate includes a lower electrode on the fourth principal plane and further includes a through-wire electrically connecting the guard ring of the third principal plane and the lower electrode. The external terminal of the optical element is electrically connected to the lower electrode via the connection electrode, the seal ring, the solder ring, the guard ring, and the through-wire.

A manufacturing method for an optical module for endoscope in another embodiment includes: a preparing step of manufacturing an optical element including a light emitting section configured to output an optical signal or a light receiving section to which the optical signal is inputted, a first wafer including a first substrate including a first principal plane and a second principal plane opposed to the first principal plane and including an annular seal on the second principal plane, and a second wafer including a second substrate including a third principal plane and a fourth principal plane opposed to the third principal plane and including an annular guard ring on the third principal plane, a recessed section surrounded by the guard ring being present on the second substrate; an optical-element mounting step of mounting the optical element on the second principal plane of the first substrate; a laminating step of bonding the seal ring of the first substrate and the guard ring of the second substrate via an annular solder ring to house the optical element in the recessed section of the second substrate and manufacturing a laminated wafer in which the recessed section is sealed up; a cutting step of cutting and singulating the laminated wafer; and a fiber fixing step of inserting an optical fiber into an insertion hole of the first principal plane of the first substrate.

DETAILED DESCRIPTION OF THE PREFERRED EMBODIMENTS

First Embodiment

Figure 1:
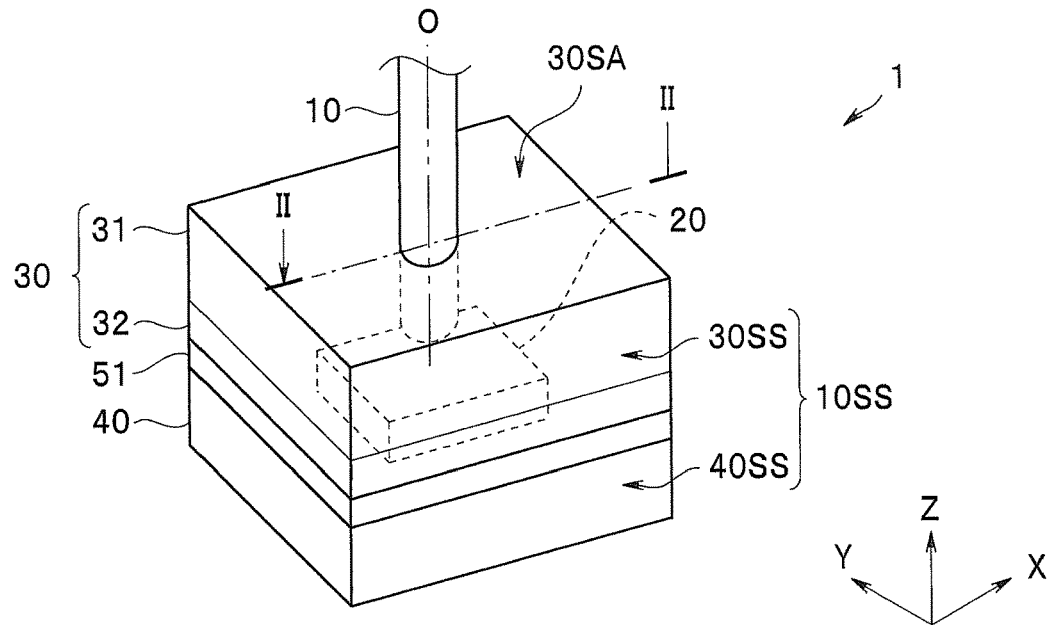
FIG. 1 is a perspective view of an optical module in a first embodiment.

An optical module for endoscope 1 (hereinafter referred to as "optical module 1") in a first embodiment is explained with reference to FIG. 1 to FIG. 3. In the following explanation, note that drawings based on respective embodiments are schematic and relations between thicknesses and widths of respective portions, ratios of the thicknesses of the respective portions, and the like are different from actual ones. Portions having different mutual relations and ratios of dimensions may be included among the drawings. Illustrations of a part of components and assigning of reference numerals and signs to a part of the components may be omitted.

The optical module 1 is an ultra-small E/O module (an electrooptical converter) that converts an electric signal outputted by an image pickup device of an endoscope into an optical signal and transmits the optical signal.

The optical module 1 includes, as main components, an optical fiber 10, an optical element 20, a first substrate 30 having a ferrule function for holding the optical fiber 10 and mounted with the optical element 20, a second substrate 40 including a recessed section H20 in which the optical element 20 is housed, a solder ring 50 that bonds the first substrate 30 and the second substrate 40.

The optical fiber 10 that transmits an optical signal includes a core having a diameter of, for example, 50 μm that transmits the optical signal and a clad having a diameter of 125 μm that covers an outer circumference of the core.

The optical element 20 is a VCSEL (vertical cavity surface emitting laser) including a light emitting section 21 that outputs an optical signal. The ultra-small optical element 20 having a plan view dimension of 250 μm×250 μm includes, on a light emitting surface, a light emitting section 21 having a diameter of 10 μm and two external terminals 22A and 22B having a diameter of 70 μm connected to the light emitting section 21. The external terminal 22A is a GND terminal having ground potential.

Note that, in the following explanation, when each of a plurality of components having the same function is referred to, one alphabet character at an end of a sign is omitted. For example, each of the external terminals 22A and 22B is referred to as external terminal 22.

The first substrate 30 has a plan view dimension of 1000 μm×1000 μm and thickness of 500 μm. The first substrate 30 includes a first principal plane 30SA and a second principal plane 30SB opposed to the first principal plane 30SA. The first substrate 30 is a ferrule including, on the first principal plane 30SA, an opening of an insertion hole H30, into which the optical fiber 10 is inserted to depth of 450 μm, and is, at the same time, a wiring plate including, on the second principal plane 30SB, a connection electrode 34 mounted with the optical element 20.

The first substrate 30 is configured of a silicon base body 31 including a transparent silicon oxide layer 32 on the second principal plane 30SB. A bottom surface H30SA of the insertion hole H30 piercing through the base body 31 is configured by the silicon oxide layer 32. That is, the insertion hole H30 is a bottomed recessed section. The silicon oxide layer 32 is disposed by, for example, gluing or anodic bonding of a quartz glass thin plate or the like to the silicon base body 31, oxidation treatment of the silicon base body 31, or a CVD method. The silicon oxide layer 32 has translucency with respect to light having a wavelength (850 to 1600 nm) of an optical signal. For example, the silicon oxide layer 32 having thickness of 10 to 100 μm transmits 95% or more of light having a wavelength of 850 nm.

The first substrate 30 includes, on the second principal plane 30SB, a seal ring 33 and the connection electrode 34 to which the external terminal 22 of the optical element 20 is bonded. The seal ring 33 having a frame shape and a seamless annular shape is configured of a conductive metal film bonded to solder. The connection electrode 34 made of conductive metal is disposed in a region surrounded by the seal ring 33.

The second substrate 40 having thickness of 300 μm includes a third principal plane 40SA and a fourth principal plane 40SB opposed to the third principal plane 40SA. The second substrate 40 includes, on the third principal plane 40SA, a guard ring 43 configured of a conductive metal film bonded to solder and includes an upper electrode 44 and a recessed section H40 in a region surrounded by the guard ring 43. The guard ring 43 having substantially the same configuration as the configuration of the seal ring 33 is disposed to be opposed to the seal ring 33 and bonded to the seal ring 33 without a gap via the solder ring 50. Although not shown in FIG. 3 and the like, peripheries of the seal ring 33, the solder ring 50, and the guard ring 43 are further sealed by sealing resin 51.

A through-wire 41 pierces through the third principal plane 40SA and the fourth principal plane 40SB and connects the upper electrode 44 of the third principal plane 40SA and a lower electrode 42 of the fourth principal plane 40SB.

The optical element 20 is housed in the recessed section H40. The upper electrode 44 is bonded to the connection electrode 34 via solder 45. Therefore, the external terminal 22 of the optical element 20 is connected to the lower electrode 42 via the solder 45, the connection electrode 34, the upper electrode 44, and the through-wire 41.

The optical element 20 generates light of an optical signal along an optical axis O according to a driving signal inputted from the lower electrode 42. The optical signal is transmitted through the transparent silicon oxide layer 32, made incident on the optical fiber 10, and transmitted.

The solder ring 50 having thickness of 2 to 15 μm made of solder such as SnAg is disposed between the guard ring 43 and the seal ring 33. A space surrounded by the second principal plane 30SB of the first substrate 30, the third principal plane 40SA of the second substrate 40, and the solder ring 50 is sealed up. That is, the optical element 20 housed in an internal space of the recessed section H40 is sealed by the solder ring 50.

As explained below, the optical module 1 is manufactured in a wafer level and singulated by cutting. Therefore, cross sections in an optical axis orthogonal direction of the first substrate 30 and the second substrate 40 have the same external shape and the same size. Optical axes O of the first substrate 30 and the second substrate 40 coincide with each other. In other words, the first substrate 30 and the second substrate 40 have the same external dimension. Four side surfaces 30SS and 40SS of the first substrate 30 and the second substrate 40 are present in the same plane (a side surface loss of the optical module 1).

The optical module 1 has high productivity and small size because the first substrate 30 having the ferrule function is also manufactured in a wafer level. The optical element 20 has high reliability because the optical element 20 is sealed up in the recessed section H40.

Further, since the base body 31 of the first substrate 30 is made of silicon, as explained below, micromachining of the first substrate 30 is easy. In particular, when the insertion hole H30 is formed by a reactive ion etching method (RIE), since the silicon oxide layer 32 functions as an etching stop layer, depth control of the insertion hole H30 is easy. Since the silicon oxide layer 32 is an insulating layer, conductor layers such as the seal ring 33 and the connection electrode 34 can be directly disposed on the silicon oxide layer 32. Therefore, the optical module for endoscope 1 particularly has high productivity.

Note that, in the optical module 1 in the first embodiment, the optical element 20 is a light emitting element including the light emitting section 21 that outputs an optical signal. On the other hand, it goes without saying that, even if an optical element of an optical module is a light receiving element such as a photodiode including a light receiving section to which an optical signal is inputted, the optical module has the same effect as the optical module 1 and the like.

<Manufacturing Method>

Figure 4:
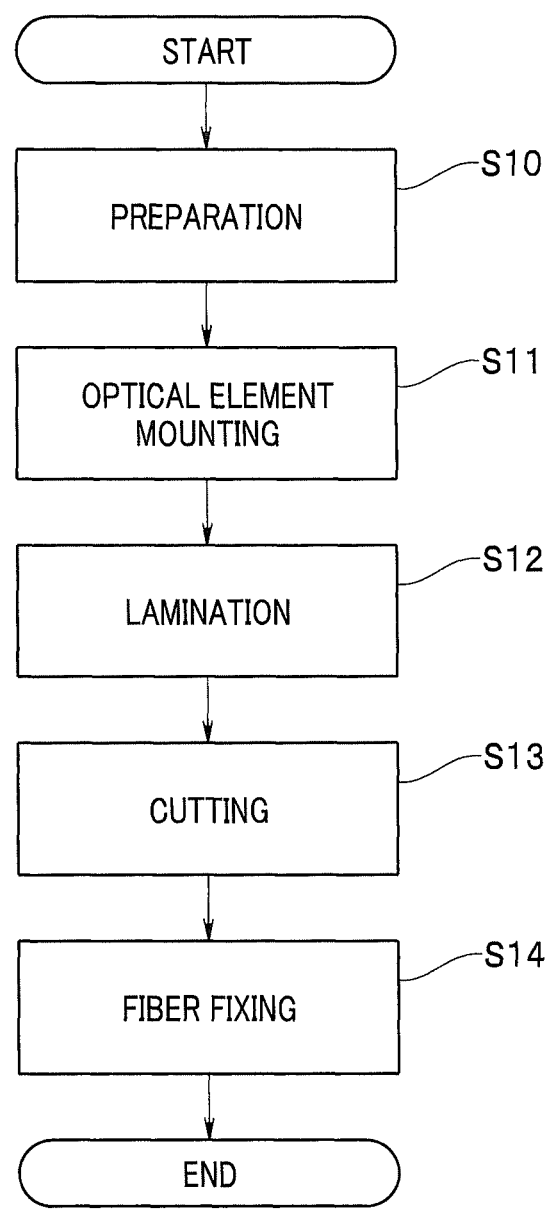
FIG. 4 is a flowchart of a manufacturing method for the optical module in the first embodiment.

A manufacturing method for the optical module 1 is explained according to a flowchart shown in FIG. 4. Note that, in the manufacturing method in this embodiment, a first wafer 30W including a plurality of first substrates 30 and a second wafer 40W including a plurality of second substrates 40 are cut after bonding.

<Step S10: Preparing Step>

A plurality of optical elements 20, the first wafer 30W including the plurality of first substrates 30, and the second wafer 40W including the plurality of second substrates 40 are manufactured. That is, the first wafer 30W is singulated into the plurality of first substrates 30 in a cutting step explained below. The second wafer 40W is singulated into the plurality of second substrates 40 in the cutting step explained below. The plurality of first substrates 30 and the plurality of second substrates 40 are respectively disposed in a matrix shape in the same manner on the first wafer 30W and the second wafer 40W.

Figure 5A:
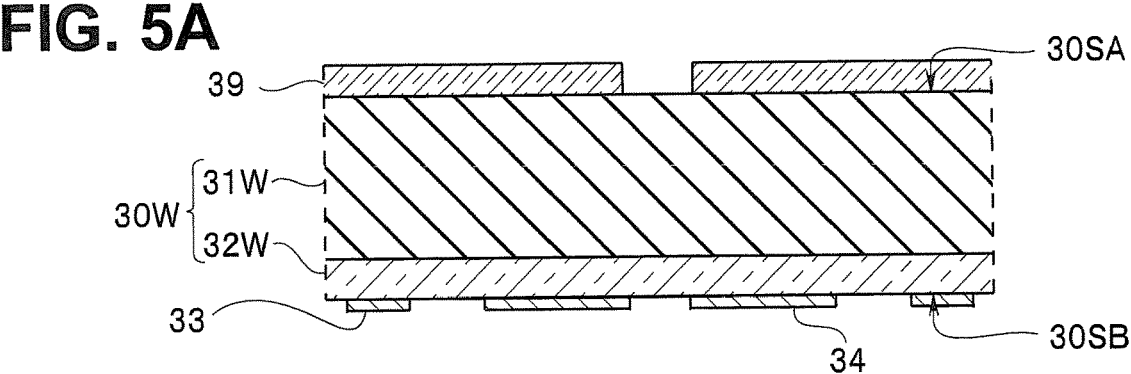
FIG. 5A is a sectional view for explaining the manufacturing method for the optical module in the first embodiment.

As shown in FIG. 5A, in the first wafer 30W, a silicon oxide layer 32W is disposed on the second principal plane 30SB of a base body wafer 31W made of silicon. The seal ring 33 is disposed on the second principal plane 30SB of the first wafer 30W. The connection electrode 34 made of gold is disposed in a region surrounded by the seal ring 33. On the first principal plane 30SA of the first wafer 30W, for example, an etching mask 39 made of a silicon oxide layer, a silicon nitride layer, or a metal layer of Cr or the like and including an opening for forming the insertion hole H30 is disposed.

Figure 5B:
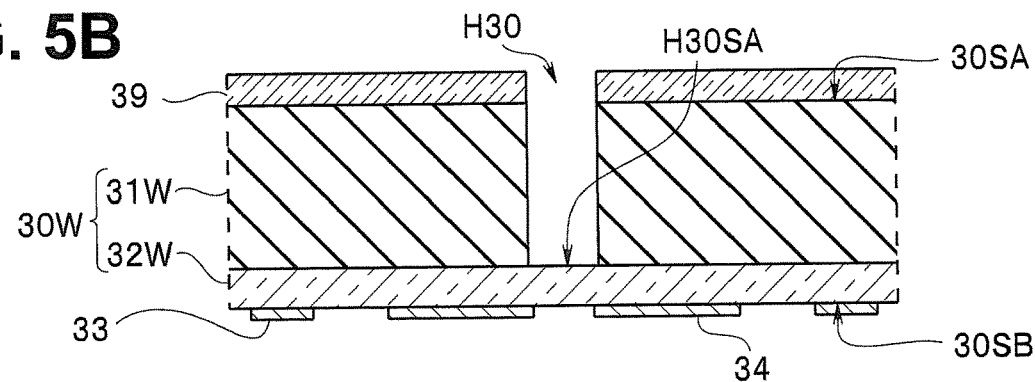
FIG. 5B is a sectional view for explaining the manufacturing method for the optical module in the first embodiment.

As shown in FIG. 5B, in the first wafer 30W, a columnar insertion hole H30 having an outer diameter and an inner diameter substantially the same as an outer diameter and an inner diameter of the optical fiber 10 inserted into the insertion hole H30 is formed by the RIE method. At this time, the silicon oxide layer 32W functions as an etching stop layer. Therefore, the insertion hole H30 having depth same as thickness of the base body wafer 31W is easily formed. The insertion hole H30 may be formed by wet etching rather than dry etching such as RIE. Besides the columnar shape, the insertion hole H30 may be formed in a square pillar shape if the optical fiber 10 can be held by an inner surface of the insertion hole H30. The insertion hole H30 may be formed in a taper shape having a diameter of an opening larger than a diameter of the bottom surface H30SA.

Note that the etching mask 39 may be disposed on the first principal plane 30SA of the first substrate 30 of the optical module 1 without being removed after the insertion hole H30 formation.

On the other hand, although not shown in the figure, the second wafer 40W and the optical element 20 that outputs an optical signal from a light emission surface are manufactured. The second wafer 40W includes the through-wire 41 and further includes the guard ring 43, the upper electrode 44 of the through-wire 41, and the recessed section H40 on the third principal plane 40SA (see FIG. 5D). The second wafer 40W is made of resin such as polyimide, ceramic, glass epoxy, glass, and silicon. The through-wire 41 is manufactured by forming a through-hole with etching or the like and thereafter disposing a conductor on an inside of the through-hole.

<Step S11: Optical-Element Mounting Step>

Figure 5C:
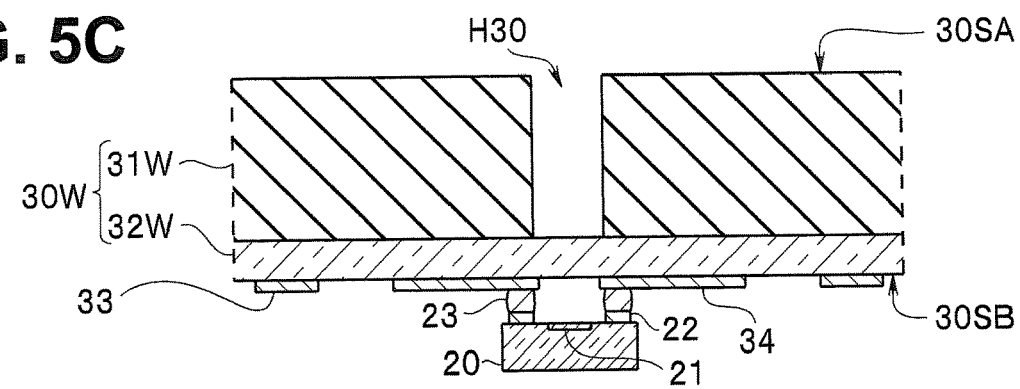
FIG. 5C is a sectional view for explaining the manufacturing method for the optical module in the first embodiment.

As shown in FIG. 5C, the external terminal 22 of the optical element 20 is bonded to the connection electrode 34 of the first wafer 30W. For example, an Au bump 23 having height of 15 μm disposed in the external terminal 22 is ultrasonic-bonded to the connection electrode 34 made of Au. Alternatively, the optical element 20 is bonded by forming AuSn solder plating of approximately 3 μm on a connection electrode and thermal compression-bonding the AuSn solder plating at temperature higher than a melting temperature of a solder ring, for example, 340° C. Note that the seal ring 33 and the connection electrode 34 may be disposed after formation of the insertion hole H30.

<Step S12: Laminating Step>

Figure 5D:
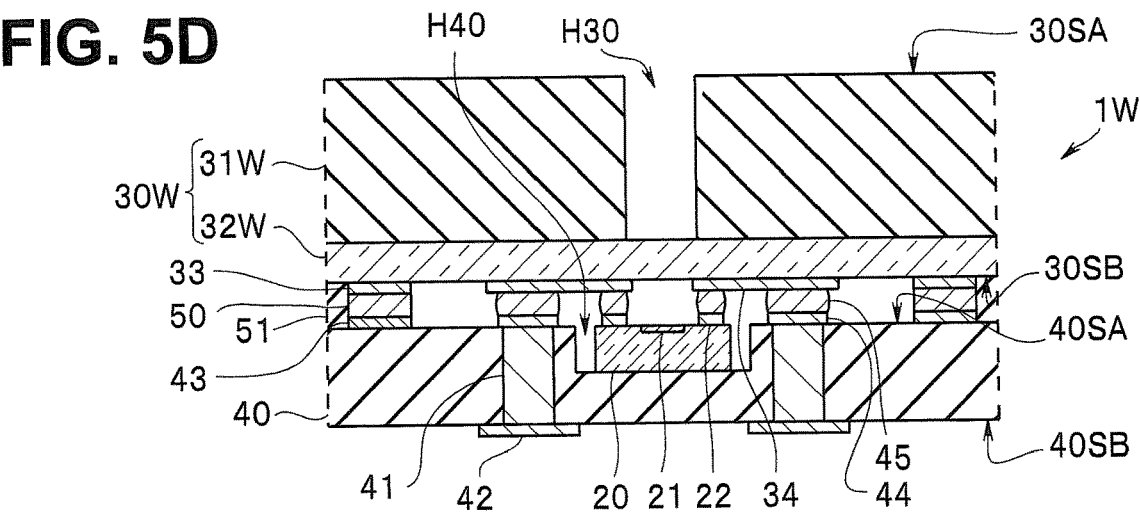
FIG. 5D is a sectional view for explaining the manufacturing method for the optical module in the first embodiment.

As shown in FIG. 5D, the first wafer 30W and the second wafer 40W are bonded via a plurality of solder rings 50 to manufacture a laminated wafer 1W.

The solder ring 50 is disposed by printing of solder paste, dispense, pattern plating, or a solder ball. However, the solder ring 50 may be disposed only on one of the seal ring 33 of the first wafer 30W and the guard ring 43 of the second wafer 40W or may be disposed on both of the seal ring 33 and the guard ring 43. Note that, when the optical element 20 is thermal compression-bonded to the connection electrode 34 via the AuSn solder, the solder ring 50 is desirably disposed on the guard ring 43 of the second wafer 40W such that the solder ring 50 does not melt during thermal compression.

The solder 45 for bonding the connection electrode 34 and the upper electrode 44 is also disposed simultaneously with the disposition of the solder ring 50.

In a state in which the first wafer 30W and the second wafer 40W are positioned and compression-bonded such that the plurality of optical elements 20 mounted on the first wafer 30W are respectively housed in a plurality of recessed sections H40 of the second wafer 40W, the first wafer 30W and the second wafer 40W are bonded by being heated to temperature exceeding the solder melting temperature.

When the first wafer 30W and the second wafer 40W are bonded, a space surrounded by the solder ring 50 is sealed up. Pressure in the recessed section H40 is equal to or lower than an atmospheric pressure when bonding treatment is performed in a decompressed state. An inert gas such as nitrogen is filled in the recessed section H40 when the bonding treatment is performed in the inert gas.

Note that depth of the recessed section H40 is desirably designed such that a rear surface opposed to the light emitting surface of the optical element 20 mounted on the first wafer 30W is in contact with a bottom surface of the recessed section H40. This is because it is easy to constantly control an interval between the first wafer 30W and the second wafer 40W.

For example, the sealing resin 51 made of silicone resin is injected and hardened around the plurality of solder rings 50 of the laminated wafer 1W. Note that the sealing resin 51 may be injected after the cutting step, may protrude to the side surface 10SS of the optical module 1, or may cover the side surface 10SS.

<Step S13: Cutting Step>

Figure 6:
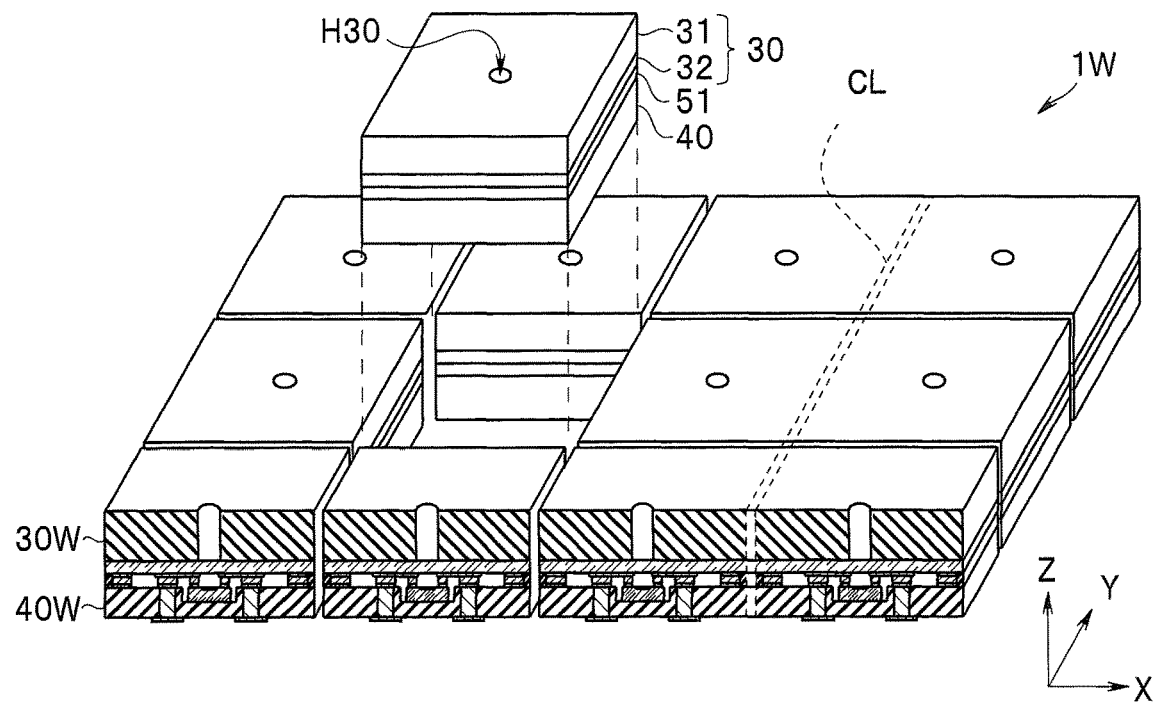
FIG. 6 is a partial sectional perspective view for explaining the manufacturing method for the optical module in the first embodiment.

As shown in FIG. 6, the laminated wafer 1W obtained by bonding the first wafer 30W and the second wafer 40W is cut along a cutting line CL and singulated. For the cutting, a dicing apparatus including a blade, a high-power laser beam machine, or the like is used.

<Step S14: Fiber Fixing Step>

Figure 2A:
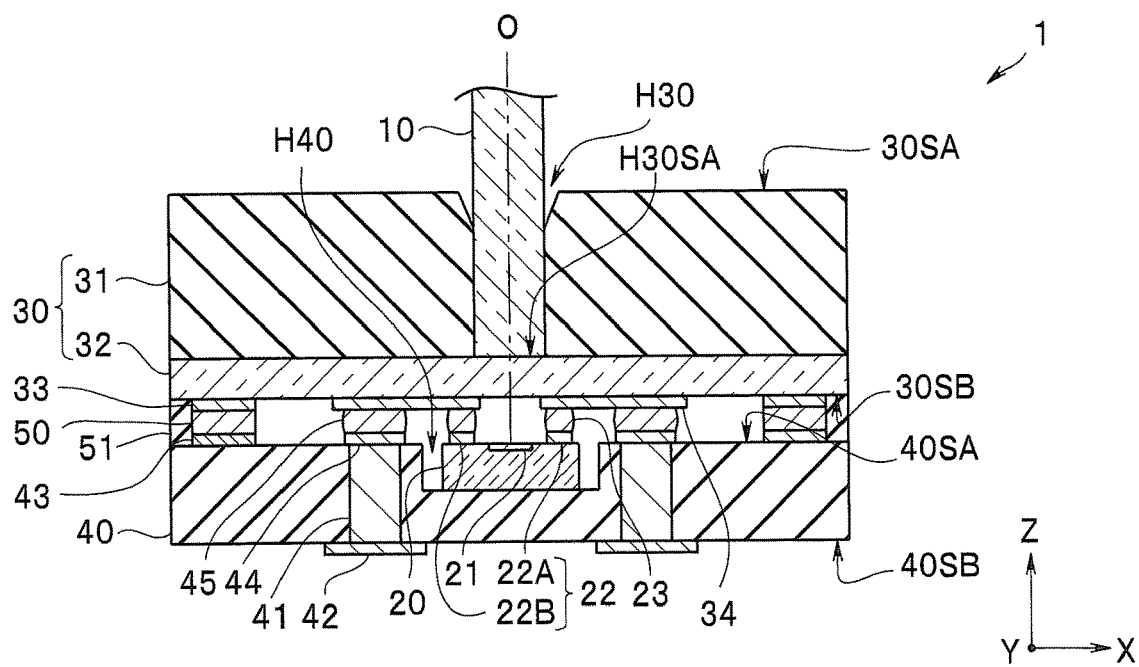
FIG. 2A is a sectional view of the optical module in the first embodiment taken along a II-II line of FIG. 1.
Figure 2B:
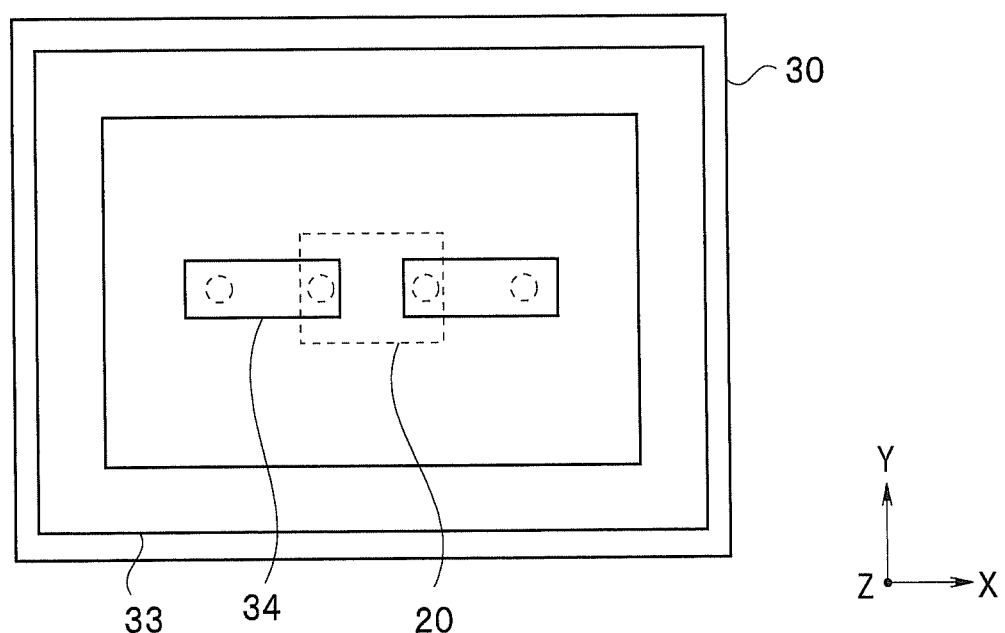
FIG. 2B is a plan view of a second principal plane of a first substrate of the optical module in the first embodiment.
Figure 3:
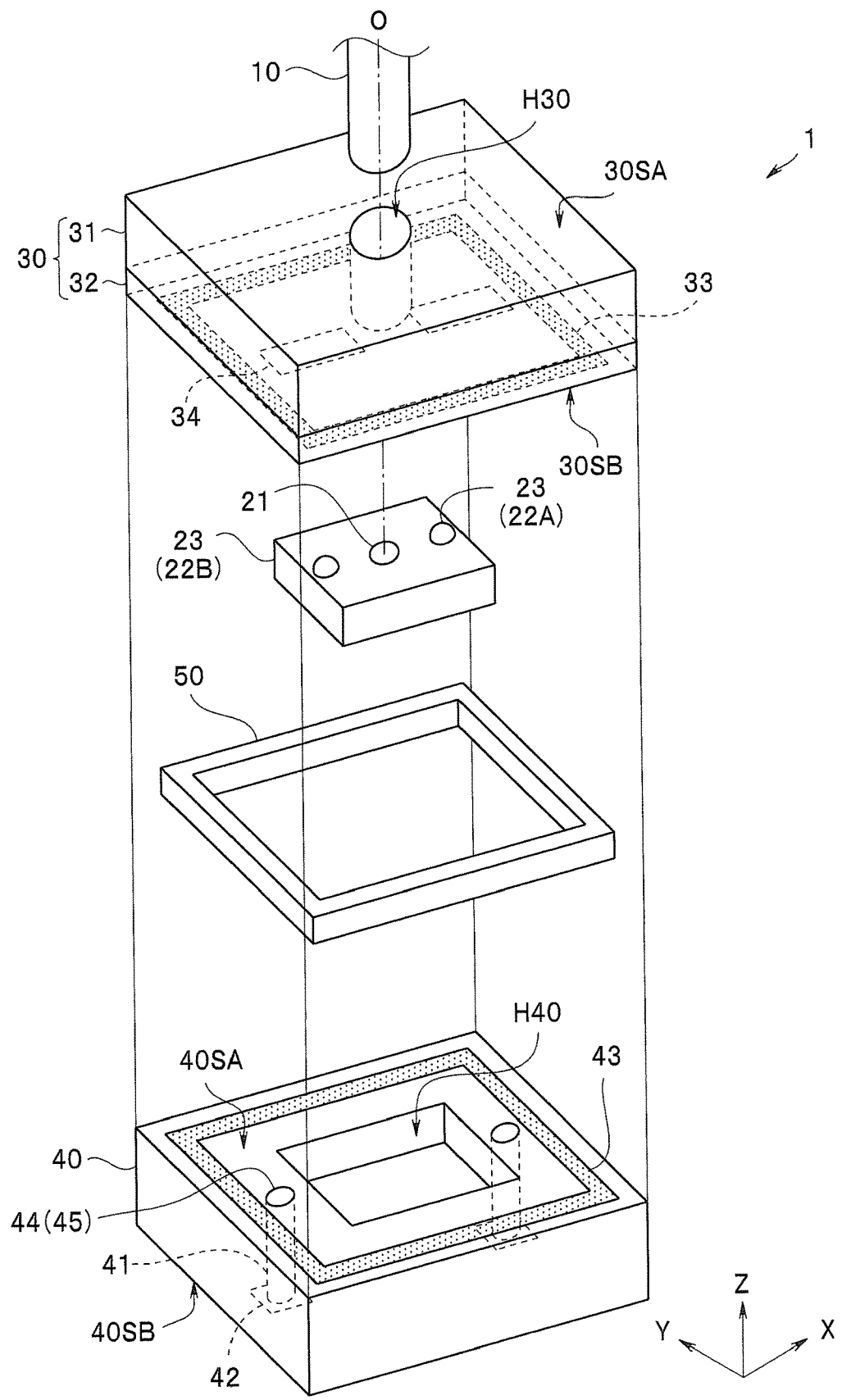
FIG. 3 is an exploded view of the optical module in the first embodiment.

When the optical fiber 10 is inserted and fixed in the insertion hole H30 of the first principal plane 30SA of the first substrate 30, the optical module for endoscope 1 shown in FIG. 1 and FIG. 2A is completed. For example, the optical fiber 10 is fixed to the first principal plane 30SA of the first substrate 30 by an adhesive (not shown in the figure). Transparent resin may be filled between a distal end of the optical fiber 10 and the bottom surface H30SA of the insertion hole H30.

Note that the sealing resin 51 is not an indispensable component. The solder ring 50 may be exposed to the side surface 10SS.

Figure 7:
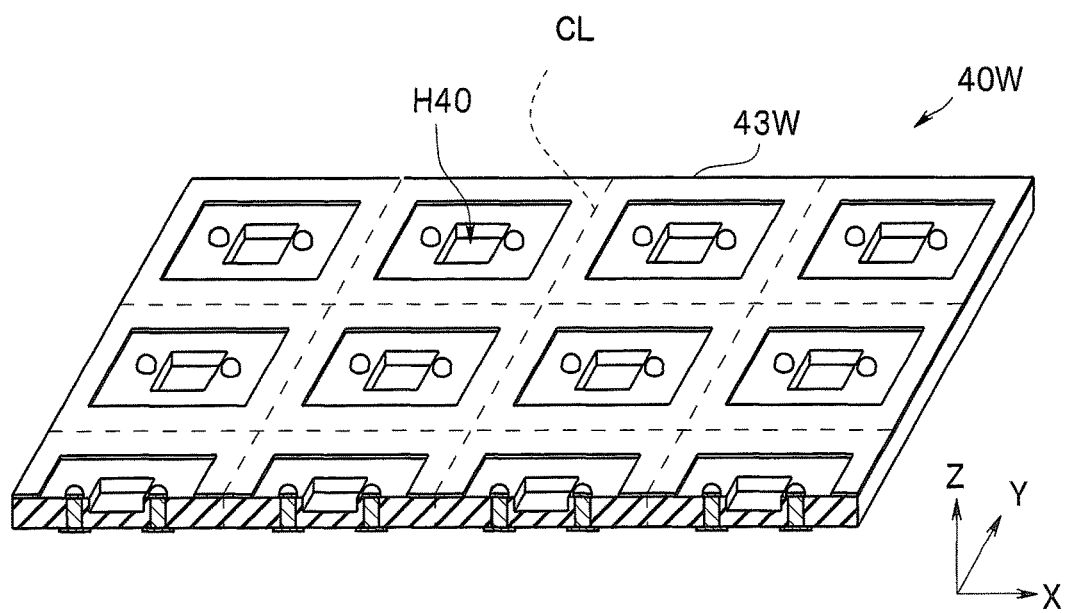
FIG. 7 is a partial sectional perspective view of a second wafer in a modification of the first embodiment.

That is, in a laminated wafer obtained by laminating the second wafer 40W and the like shown in FIG. 7, a guard ring film 43W is cut along the cutting line CL by the cutting step to be an annular guard ring. As in the second wafer 40W, in the first wafer 30W, a seal ring film is cut to be an annular seal ring or a solder film having the same shape as the guard ring film 43W and the seal ring film is cut to be an annular solder ring. Therefore, cut surfaces of the guard ring, the solder ring, and the seal ring are exposed to the side surface loss of the optical module 1.

According to this embodiment, it is possible to provide a manufacturing method for an optical module for endoscope having high reliability, small size, and high productivity.

Modification of the First Embodiment

An optical module for endoscope 1A in a modification of the first embodiment is similar to the optical module 1 and has the same effect as the effect of the optical module 1. Therefore, components having the same functions are denoted by the same reference numerals and signs. Explanation of the components is omitted.

Figure 8:
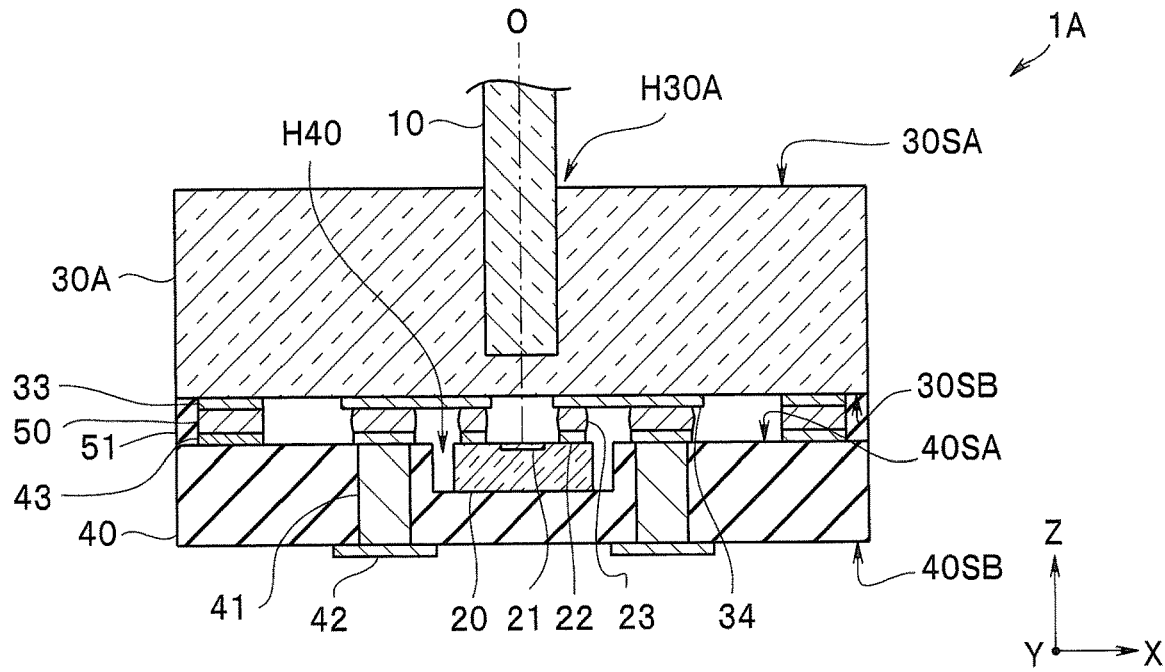
FIG. 8 is a sectional view of an optical module in a modification 1 of the first embodiment.

In the optical module 1A in a modification 1 shown in FIG. 8, a first substrate 30A is made of a transparent material, for example, glass or optical resin such as polycarbonate. An insertion hole H30A is a recessed section formed on the first substrate 30A.

Note that the first substrate 30A only has to be configured by a material substantially transparent with respect to a wavelength of light of an optical signal. For example, when the wavelength of the optical signal is in a visible light region, the first substrate 30A is made of glass, polycarbonate resin, or the like. When the light of the optical signal is infrared light, the first substrate 30A may be configured by, for example, silicon that does not transmit visible light but transmits the infrared light.

For example, an etching time of the optical module 1A needs to be accurately managed in order to form the insertion hole H30A having desired depth. However, it is easier to manufacture the first substrate 30A than the first substrate 30 of the optical module 1.

Second Embodiment

An optical module for endoscope 1B in a second embodiment is similar to the optical module 1 and has the same effect as the effect of the optical module 1. Therefore, components having the same functions are denoted by the same reference numerals and signs. Explanation of the components is omitted.

Figure 9A:
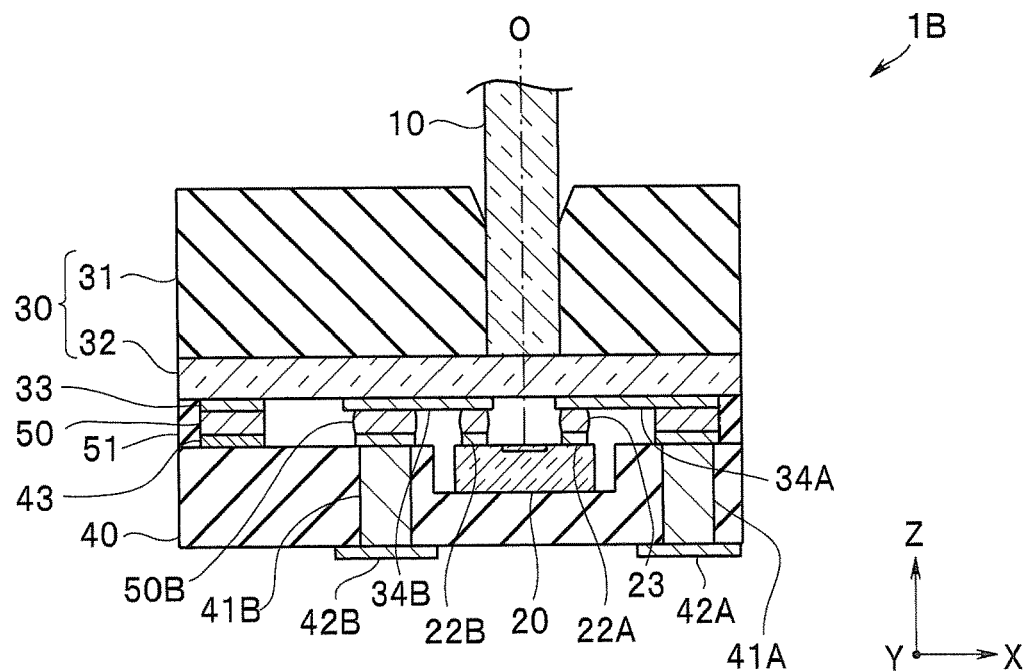
FIG. 9A is a sectional view of an optical module in a second embodiment.

In the optical module 1B shown in FIG. 9A, a connection electrode 34A bonded to the external terminal 22A having ground potential of the optical element 20 is extended to the seal ring 33. For example, a connection electrode 34B and the seal ring 33 are simultaneously formed as an integrated object with the same material and disposed. A through-wire 41B of a second substrate 40B is connected to the guard ring 43 (the solder ring 50).

Figure 10:
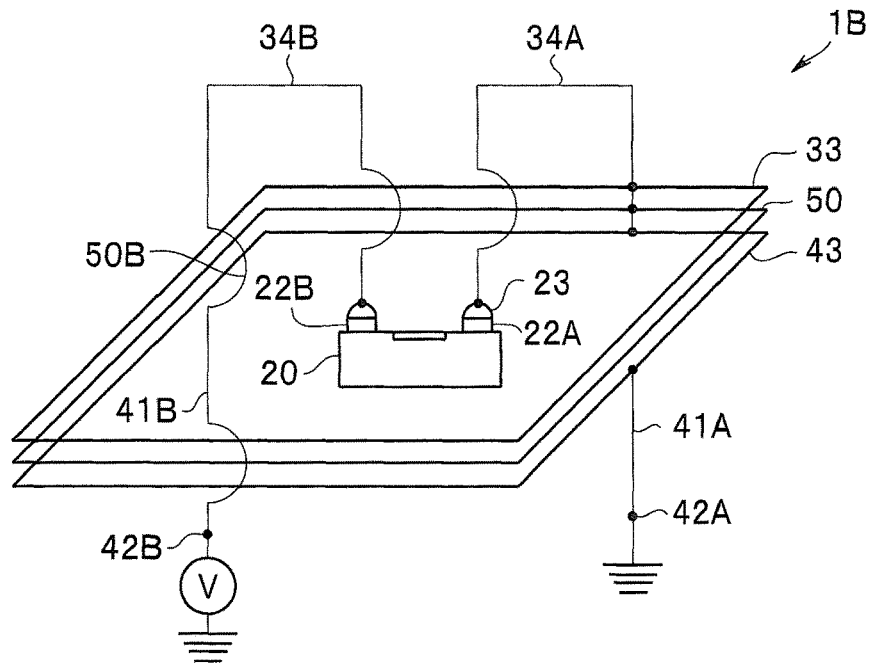
FIG. 10 is an electric wiring diagram of the optical module in the second embodiment.

That is, as shown in FIG. 10, the external terminal 22A of the optical element 20 is electrically connected to a lower electrode 42A via the bump 23, the connection electrode 34A, the seal ring 33, the solder ring 50, the guard ring 43, and a through-wire 41A. A ground potential line is connected to the lower electrode 42A.

On the other hand, the external terminal 22B of the optical element 20 is electrically connected to a lower electrode 42B via the bump 23, the connection electrode 34B, solder 50B, and the through-wire 41B. A driving signal line is connected to the lower electrode 42B.

In a manufacturing method for the optical module 1B, in a laminating step, the external terminal 22A is electrically connected to the lower electrode 42A.

Figure 9B:
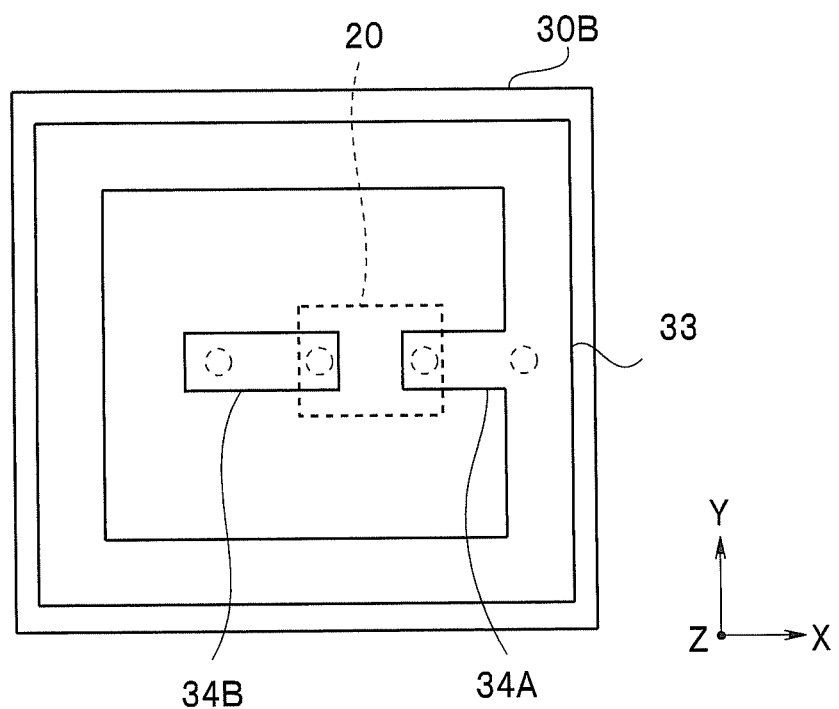
FIG. 9B is a plan view of a second principal plane of a first substrate of the optical module in the second embodiment.

The optical module 1B has a simpler configuration than the optical module 1. The solder ring 50 connected to the connection electrode 34A performs both of electric connection and sealing. Unlike the optical module 1 shown in FIG. 2B, in the optical module 1B, the space between the connection electrode 34 and the solder ring 50 is unnecessary. Therefore, as shown in FIG. 9B, the optical module 1B is smaller than the optical module 1. The seal ring 33, the solder ring 50, and the guard ring 43 have the ground potential. The external terminal 22A of the optical element 20 is connected to a ground potential line by a short path. Therefore, the optical module 1B is less easily affected by external noise.

Modifications of the Second Embodiment

Optical modules for endoscope 1C to 1E in modifications of the second embodiment are similar to the optical modules 1 and 1B and have the same effect as the effect of the optical modules 1 and 1B. Therefore, components having the same functions are denoted by the same reference numerals and signs. Explanation of the components is omitted.

Modification 1 of the Second Embodiment

Figure 11:
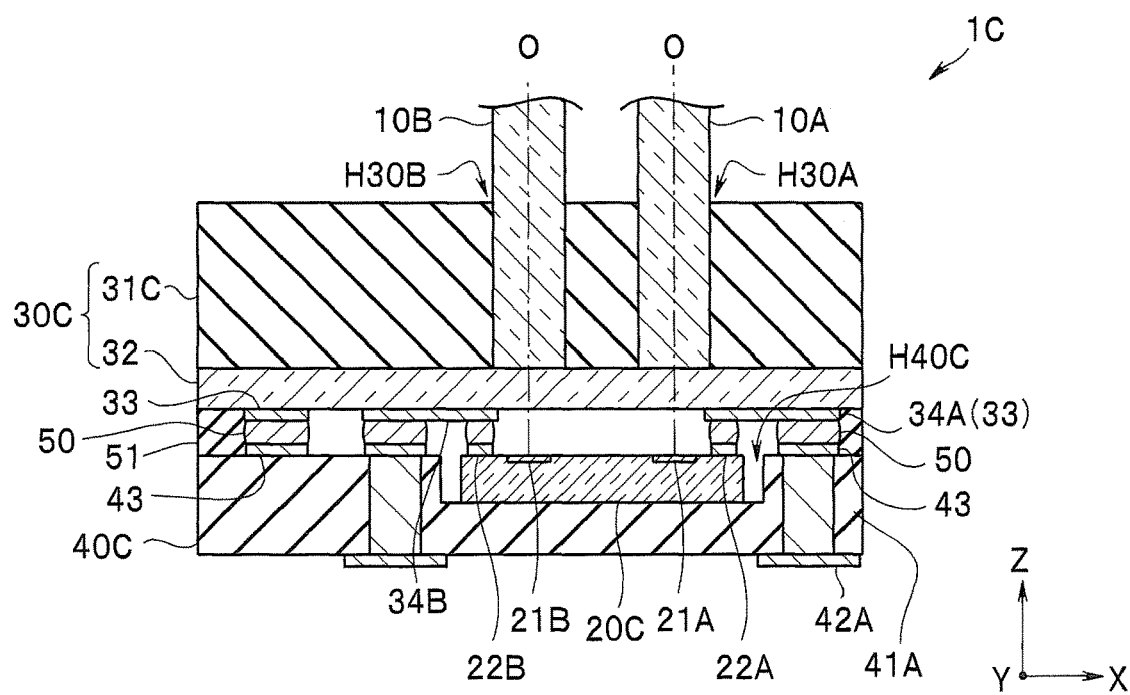
FIG. 11 is a sectional view of an optical module in a modification 1 of the second embodiment.

In the optical module for endoscope 1C shown in FIG. 11, an optical element 20C is an array-type optical element including a plurality of light emitting sections 21A and 21B. The optical module for endoscope 1C includes a plurality of optical fibers 10A and 10B. A plurality of insertion holes H30A and H30B are present in a base body 31C of a first substrate 30C.

For example, the light emitting section 21A emits light with a driving signal A applied to the second external terminal 22B by a ground potential line with which the first external terminal 22A is connected to the solder ring 50. The light emitting section 21B emits light with a driving signal B applied to a not-shown third external terminal.

Note that an optical element may include a light emitting section and a light receiving section or a plurality of light receiving sections. That is, the optical element may be an array-type optical element including a light emitting section and a light receiving section, a plurality of light emitting sections, or a plurality of light receiving sections. A total number of the light emitting sections and the light receiving sections may be three or more. The light emitting sections and the light receiving sections may include four or more external terminals.

Modification 2 of the Second Embodiment

Figure 12:
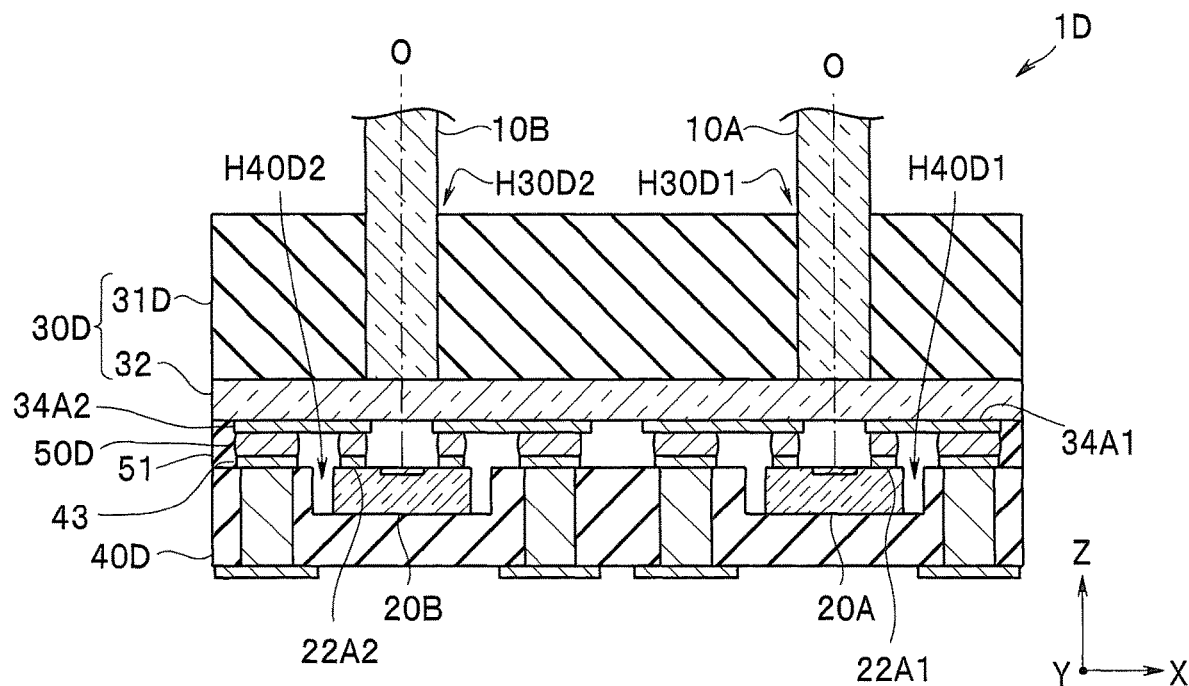
FIG. 12 is a sectional view of an optical module in a modification 2 of the second embodiment.

The optical module for endoscope 1D shown in FIG. 12 includes optical elements 20A and 20B and the optical fibers 10A and 10B. Insertion holes H30D1 and H30D2 are present in a base body 31D of a first substrate 30D. Recessed sections H40D1 and H40D2 are present on a second substrate 40D.

An optical signal of the optical element 20A housed in the recessed section H40D1 is made incident on the optical fiber 10A inserted into the insertion hole H30D1. An optical signal of the optical element 20B housed in the recessed section H40D2 is made incident on the optical fiber 10B inserted into the insertion hole H30D2. External terminals 22A1 and 22A2 having ground potential of the optical elements 20A and 20B are connected to a solder ring 50D via respective connection electrodes 34A1 and 34A2.

The optical elements 20A and 20B are sealed by one solder ring 50D. That is, the recessed sections H40D1 and H40D2 are disposed in a region surrounded by the solder ring 50D.

Note that the optical elements 20A and 20B may be housed in one recessed section disposed in a region surrounded by a solder ring.

An optical module may include a light emitting element and a light receiving element or a plurality of light receiving elements sealed by one solder ring.

That is, the optical module may include a plurality of optical fibers and a plurality of optical elements. The plurality of optical elements may be sealed by one solder ring. A total number of the light emitting elements and the light receiving elements may be three or more.

Modification 3 of the Second Embodiment

Figure 13:
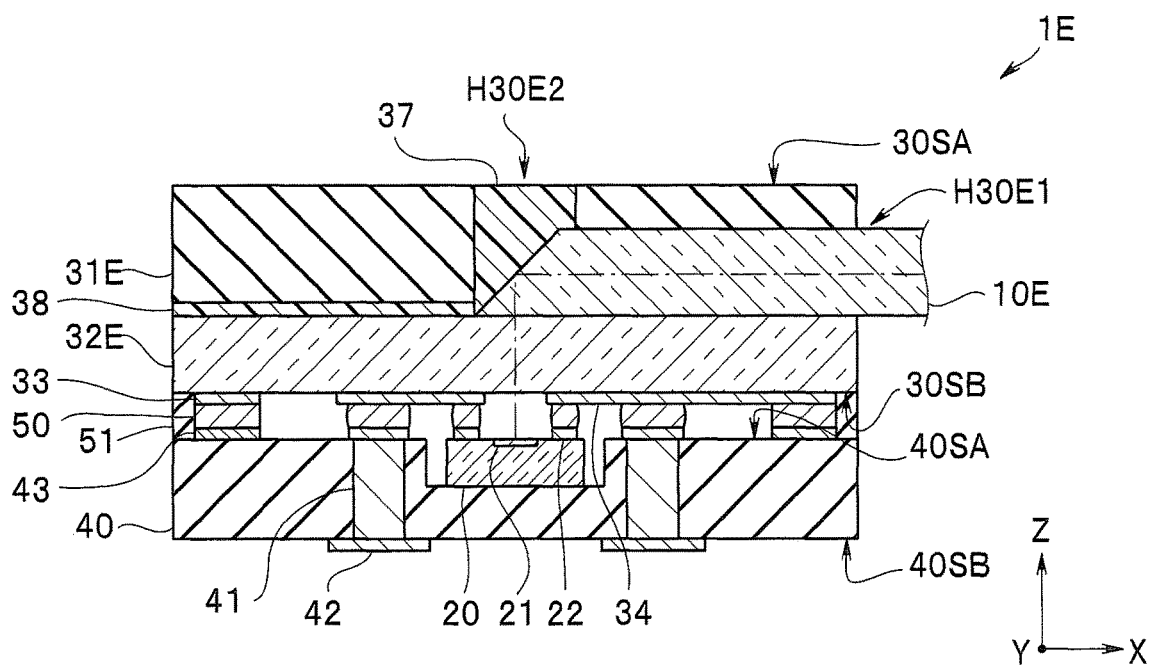
FIG. 13 is a sectional view of an optical module in a modification 3 of the second embodiment.

As shown in FIG. 13, the optical module for endoscope 1E further includes a ferrule 31E including an insertion hole 30H into which the optical fiber 10 is inserted. The ferrule 31E is disposed on the first principal plane 30SA of a transparent first substrate 32E via a bonding layer 38.

That is, an insertion hole H30E1 into which an optical fiber 10E is inserted in parallel to the principal plane 30SA is formed on a side surface of the ferrule 31E. A distal end of the optical fiber 10E is formed as a reflection surface having an inclination angle of approximately 45 degrees. In the ferrule 31E, a hole H30E2 communicating with the insertion hole H30E1 is formed on the principal plane 30SA. Resin 37 that fixes the optical fiber 10E is filled in the hole H30E2.

The optical module 1E is manufactured by cutting of a laminated wafer obtained by laminating, together with a first wafer and a second wafer, a ferrule wafer including a plurality of ferrules. Therefore, the ferrule 31E, the first substrate 32E, and the second substrate 40 have the same external dimension in the optical axis orthogonal direction. Side surfaces of the ferrule 31E, the first substrate 32E, and the second substrate 40 are present in the same plane.

Like the optical module 1, the optical module 1E is small and has high productivity. Flexibility of design of the optical module 1E is increased because the optical fiber 10E can be disposed in parallel to a substrate on which the optical module 1E is surface-mounted.

Note that, in the optical module 1, as in the optical module 1E, an optical fiber, a distal end of which is formed as a reflection surface, may be inserted into an insertion hole having an opening on a side surface. Instead of the first substrate 30, a ferrule may be disposed on the transparent first substrate 32E via a bonding layer.

In the embodiments and the modifications explained above, for example, as shown in FIG. 6, the first wafer 30W and the second wafer 40W are manufactured by a method of cutting the bonded laminated wafer 1W.

However, a (chip to wafer) method of bonding one of a first substrate and a second substrate in a wafer state and the other in a chip state obtained by singulating a wafer may be adopted. A (chip to chip) method of bonding a first substrate and a second substrate in the chip state obtained by cutting and singulating a wafer may be adopted.

<Third Embodiment and Fourth Embodiment> The (Chip to Wafer) Method

Figure 14:
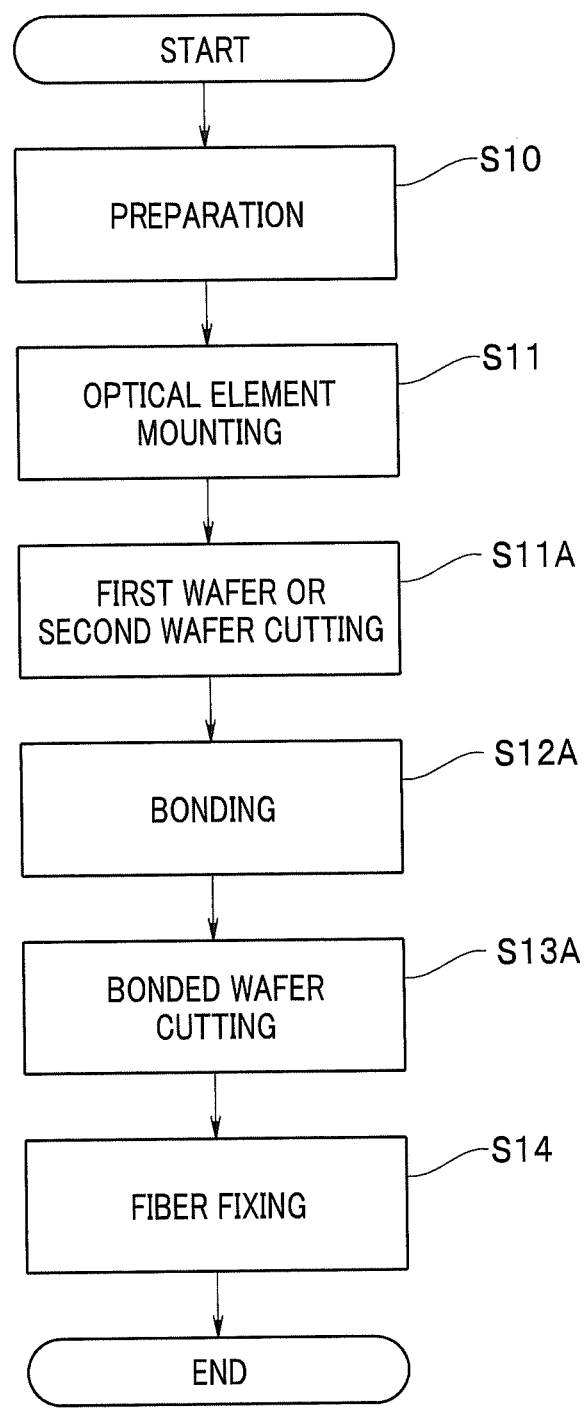
FIG. 14 is a flowchart of a manufacturing method for an optical module in a third embodiment and a fourth embodiment.

A flowchart of a manufacturing method for an optical module 1F in a third embodiment and an optical module 1G in a fourth embodiment is shown in FIG. 14.

Figure 15A:
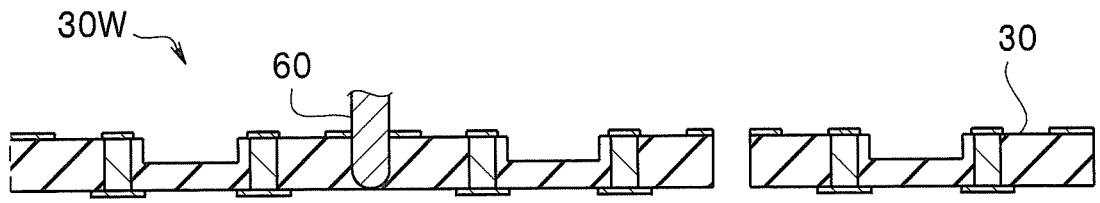
FIG. 15A is a sectional view for explaining the manufacturing method for the optical module in the third embodiment.
Figure 16A:
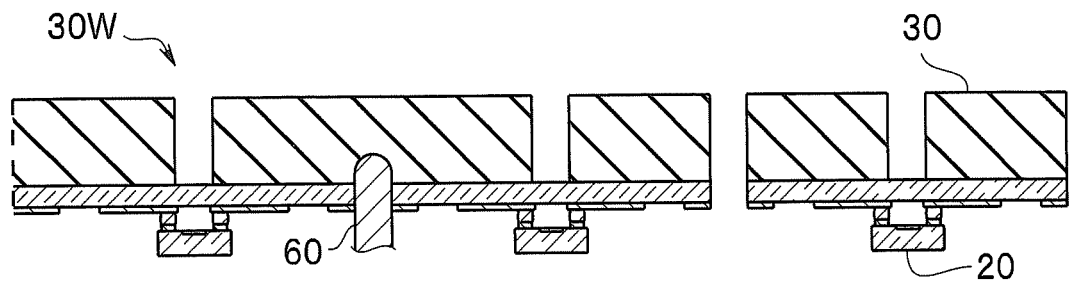
FIG. 16A is a sectional view for explaining the manufacturing method for the optical module in the fourth embodiment.

As shown in FIG. 15A or FIG. 16A, a cutting step S11A is performed before a laminating step A12A. The first wafer 30W or the second wafer 40W is singulated into the first substrates 30 or the second substrates 40 by a dicing blade 60.

Figure 15B:
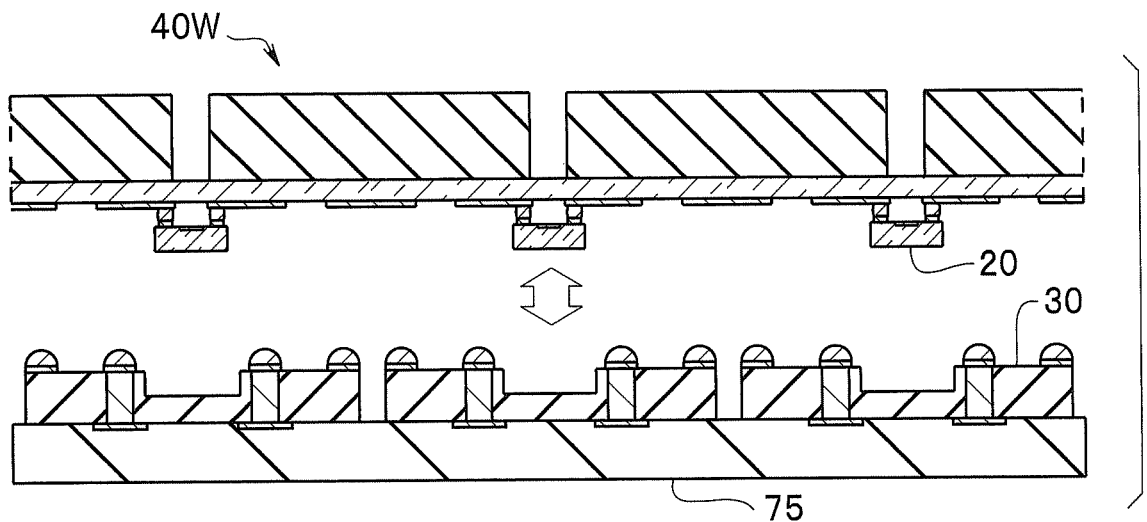
FIG. 15B is a sectional view for explaining the manufacturing method for the optical module in the third embodiment.
Figure 16B:
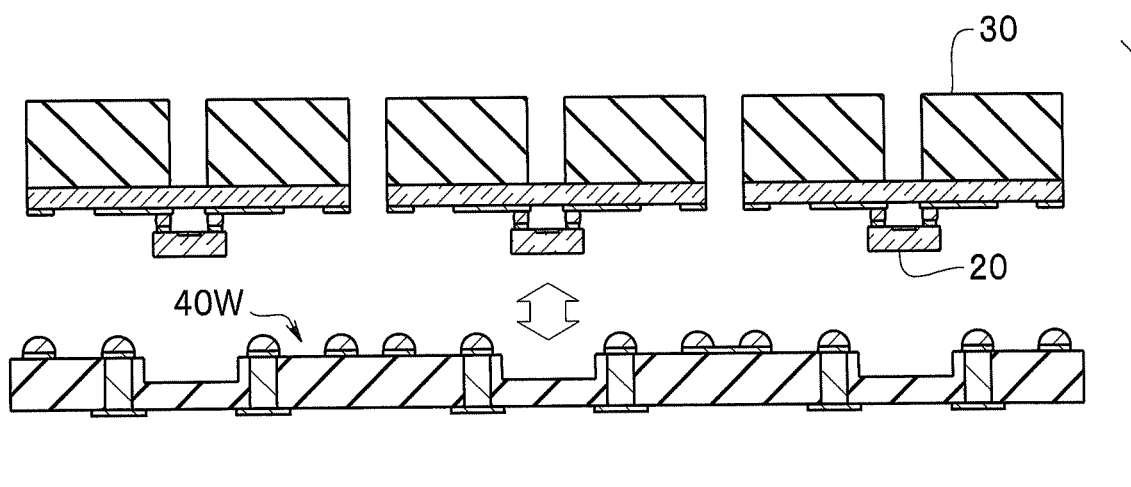
FIG. 16B is a sectional view for explaining the manufacturing method for the optical module in the fourth embodiment.

In a bonding step S12A, as shown in FIG. 15B, the singulated second substrates 40 in the chip state are solder-bonded to the first substrate (the first wafer 30W) in the wafer state. Alternatively, as shown in FIG. 16B, the singulated first substrates 30 in the chip state are solder-bonded to the second substrate (the second wafer 40W) in the wafer state.

Note that the plurality of second substrates 40 can be simultaneously bonded to the first wafer 30W by disposing the plurality of second substrates 40 on a support jig 75, then bringing the plurality of second substrates 40 into contact with the first wafer 30W and performing heating treatment (e.g., reflow treatment) as illustrated in FIG. 15B. Similarly, the plurality of first substrates 30 can be simultaneously bonded to the second wafer 40W.

Figure 15C:
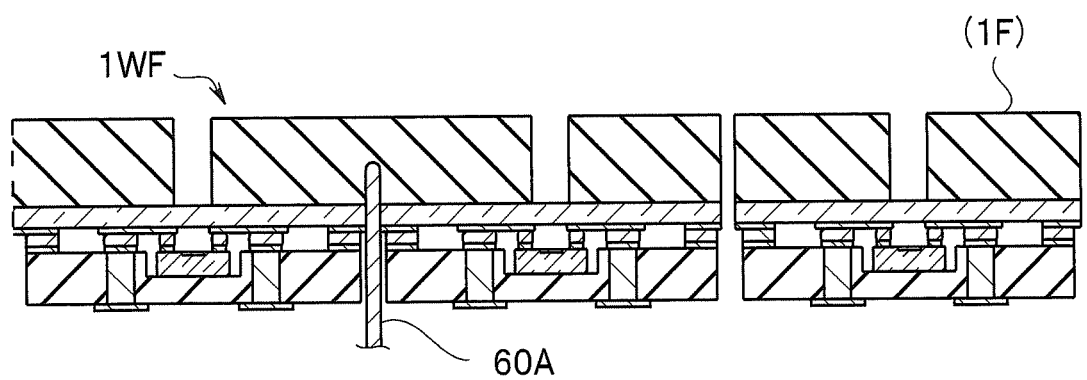
FIG. 15C is a sectional view for explaining the manufacturing method for the optical module in the third embodiment.
Figure 16C:
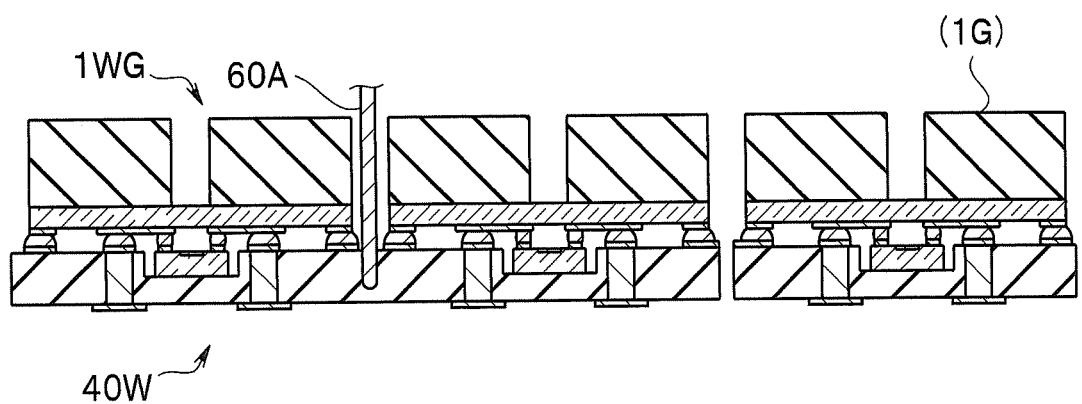
FIG. 16C is a sectional view for explaining the manufacturing method for the optical module in the fourth embodiment.

In a bonded-wafer cutting step (S13A), as shown in FIG. 15C, the first wafer 30W (a bonded wafer 1WF) to which the plurality of second substrates 40 are bonded is singulated using a dicing blade 60A. Alternatively, as shown in FIG. 16C, the second wafer 40W (a bonded wafer 1WG) to which the plurality of first substrates 30 are bonded is singulated using the dicing blade 60A.

Although not shown in the figures, the optical module 1F or the optical module 1G is completed through the fiber fixing step S14.

Note that, since the singulated second substrates 40 are bonded not to overlap dicing lines of the first wafer 30W, a cutting target is the first wafer 30W. Cutting thickness is reduced. This leads to reduction in cutting time and a higher yield.

<Fifth Embodiment> The Chip to Chip Method

Figure 17:
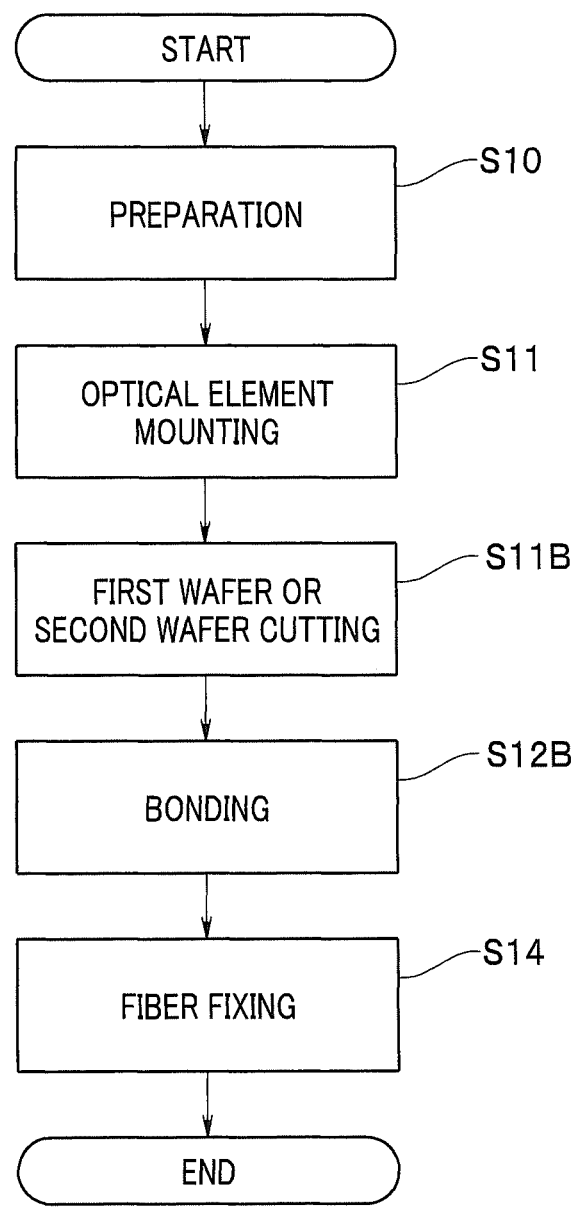
FIG. 17 is a flowchart of a manufacturing method for an optical module in a fifth embodiment.

A flowchart of a manufacturing method for an optical module 1H in a fifth embodiment is shown in FIG. 17.

Figure 18A:
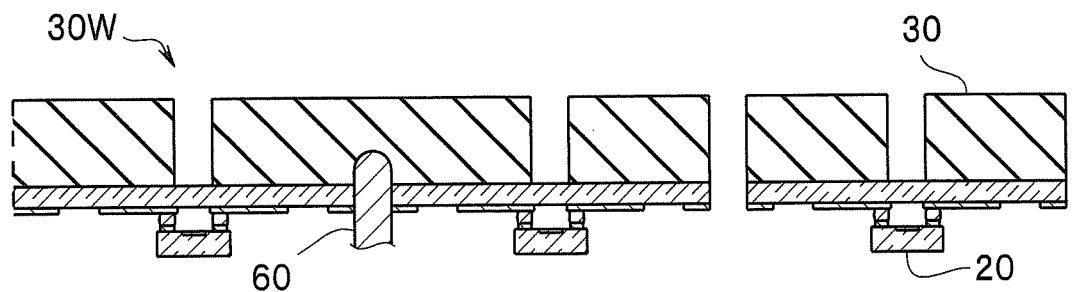
FIG. 18A is a sectional view for explaining the manufacturing method for the optical module in the fifth embodiment.
Figure 18B:
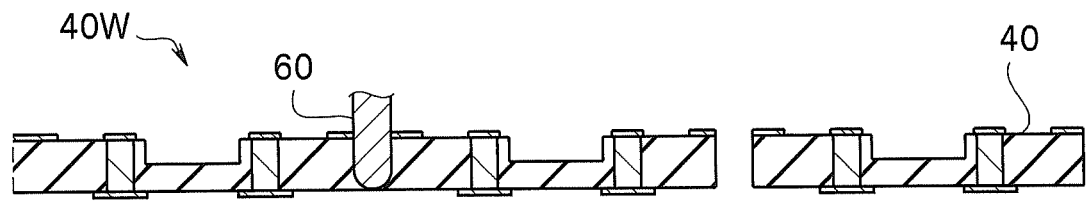
FIG. 18B is a sectional view for explaining the manufacturing method for the optical module in the fifth embodiment.
Figure 18C:
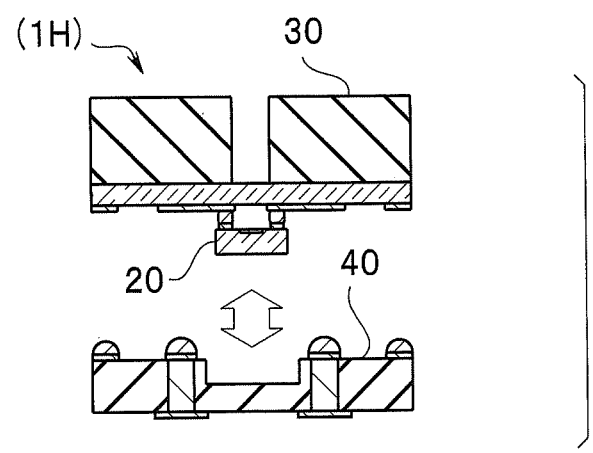
FIG. 18C is a sectional view for explaining the manufacturing method for the optical module in the fifth embodiment.

In a cutting step S11B, as shown in FIG. 18A, the first wafer 30W is singulated into the first substrates 30. As shown in FIG. 18B, the second wafer 40W is singulated into the second substrates 40. In a laminating step, the first substrates 30 and the second substrates 40 are bonded.

Although not shown in the figure, the optical module 1H is completed through the fiber fixing step S14.

As explained above, in the case of the chip to wafer method or the chip to chip method, respective external shapes of the first substrates 30 and the second substrates 40 after the singulation may not be the same. An external shape and an area of one of the first substrates 30 and the second substrates 40 may be larger or smaller than the other.

Sixth Embodiment

An endoscope 9 in a sixth embodiment is explained. The endoscope 9 includes the optical module 1 (1A to 1E) at a distal end portion 9A of an insertion section 9B.

Figure 19:
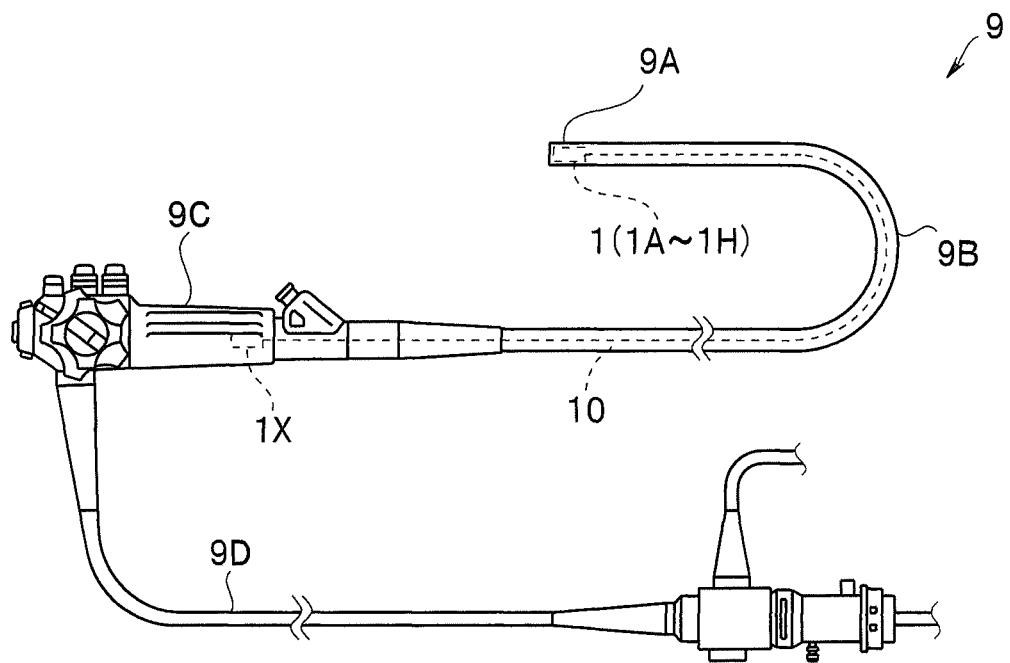
FIG. 19 is a perspective view of an endoscope in a sixth embodiment.

That is, as shown in FIG. 19, the endoscope 9 includes the insertion section 9B in which an image pickup section including an image pickup device having a large number of pixels is disposed at the distal end portion 9A, an operation section 9C disposed on a proximal end side of the insertion section 9B, and a universal cord 9D extending from the operation section 9C.

An electric signal outputted by the image pickup section is converted into an optical signal by the optical module 1 (1A to 1E), in which an optical element is a surface emitting laser, converted into an electric signal again by an optical module 1X, in which an optical element is a PD, disposed in the operation section 9C via the optical fiber 10, and transmitted via a metal wire. That is, a signal is transmitted via the optical fiber 10 in the small-diameter insertion section 9B.

As explained above, the optical module 1 (1A to 1H) has high optical coupling efficiency, small size, and high productivity. Since the optical element 20 is sealed up by the solder ring 50 having lower absorbency than resin, the optical module 1 (1A to 1H) has high resistance against a high-temperature and high-humidity test and an autoclave test and thus has high reliability. Therefore, the endoscope 9 has high optical transmission efficiency, high reliability, small size, and high productivity.

Note that the optical module 1X is disposed in the operation section 9C having a relatively wide disposition space. However, the optical module 1X desirably has the same configuration as the configuration of the optical module 1 and the like of the present invention. The endoscope 9 is a flexible endoscope but may be a rigid endoscope. A control signal to the image pickup section may be converted into an optical signal by the optical module 1 (1A to 1E) disposed in the operation section 9C. An optical signal may be converted into an electric signal by the optical module 1X disposed at the distal end portion 9A.

The present invention is not limited to the respective embodiments explained above. Various changes, combinations, and applications are possible within a range not departing from the gist of the invention.

What is claimed is:

1. An optical module for endoscope comprising:
    an optical element including a light emitting section configured to output an optical signal from an optical fiber or a light receiving section to which the optical signal is inputted and an external terminal connected to the light emitting section or the light receiving section;
    a first substrate including a first principal plane and a second principal plane opposed to the first principal plane, an insertion hole into which the optical fiber is inserted being present on the first principal plane and the optical element being mounted on the second principal plane;
    a second substrate including a third principal plane and a fourth principal plane opposed to the third principal plane, a recessed section in which the optical element is housed being present on the third principal plane; and
    a solder ring configured to bond an annular seal ring of the second principal plane of the first substrate and an annular guard ring of the third principal plane of the second substrate and seal up the recessed section, wherein
    the first substrate includes, on the second principal plane, a connection electrode disposed on an inner side of the seal ring, the connection electrode electrically connecting the external terminal of the optical element and the seal ring,
    the second substrate includes a lower electrode on the fourth principal plane and further includes a through-wire electrically connecting the guard ring of the third principal plane and the lower electrode, and
    the external terminal of the optical element is electrically connected to the lower electrode via the connection electrode, the seal ring, the solder ring, the guard ring, and the through-wire.

2. The optical module for endoscope according to claim 1, wherein the first substrate and the second substrate have a same external dimension in an optical axis orthogonal direction, and side surfaces of the first substrate and the second substrate are present in a same plane.

3. The optical module for endoscope according to claim 1, wherein the first substrate is made of a material substantially transparent with respect to a wavelength of light of the optical signal.

4. The optical module for endoscope according to claim 1, wherein
    the first substrate is made of silicon including, on the second principal plane, a silicon oxide layer translucent with respect to light having a wavelength of the optical signal, and
    a bottom surface of the insertion hole is configured by the silicon oxide layer.

5. An endoscope comprising the optical module for endoscope according to claim 1.

6. The optical module for endoscope according to claim 1, further comprising the optical fiber configured to transmit the optical signal.

7. The optical module for endoscope according to claim 6, wherein the optical element is an array-type optical element including the light emitting section and the light receiving section, a plurality of light emitting sections, or a plurality of light receiving sections and includes a plurality of optical fibers.

8. The optical module for endoscope according to claim 6, comprising a plurality of optical fibers and a plurality of optical elements, wherein the plurality of optical elements are sealed by a single one of the solder ring.

9. An optical module for endoscope comprising:
    an optical element including a light emitting section configured to output an optical signal from an optical fiber or a light receiving section to which the optical signal is inputted and an external terminal connected to the light emitting section or the light receiving section;
    a first substrate including a first principal plane and a second principal plane opposed to the first principal plane, the optical element being mounted on the second principal plane;

a second substrate including a third principal plane and a fourth principal plane opposed to the third principal plane, the optical element being housed in a recessed section of the third principal plane; and a solder ring configured to bond the first substrate and the second substrate, wherein an annular seal ring of the second principal plane of the first substrate and a guard ring of the third principal plane of the second substrate are bonded via the solder ring, and the recessed section is sealed up, the first substrate includes, on the second principal plane, a connection electrode disposed on an inner side of the seal ring, the connection electrode electrically connecting the external terminal of the optical element and the seal ring, the second substrate includes a lower electrode on the fourth principal plane and further includes a through-wire electrically connecting the guard ring of the third principal plane and the lower electrode, and the external terminal of the optical element is electrically connected to the lower electrode via the connection electrode, the seal ring, the solder ring, the guard ring, and the through-wire.

10. The optical module for endoscope according to claim 9, further comprising a ferrule including an insertion hole into which the optical fiber is inserted, wherein the ferrule is disposed on the first principal plane of the first substrate, and the ferrule, the first substrate, and the second substrate have a same external dimension in an optical axis orthogonal direction, and side surfaces of the ferrule, the first substrate, and the second substrate are present in a same plane.

11. The optical module for endoscope according to claim 9, wherein the first substrate is made of silicon including a silicon oxide layer on the second principal plane, and an insertion hole into which the optical fiber is inserted is present on the first principal plane, a bottom surface of the insertion hole is configured by the silicon oxide layer, and the first substrate and the second substrate have a same external dimension in an optical axis orthogonal direction, and side surfaces of the first substrate and the second substrate are present in a same plane.

12. An endoscope comprising the optical module for endoscope according to claim 9.

13. The optical module for endoscope according to claim 9, further comprising the optical fiber configured to transmit the optical signal.

14. A manufacturing method for an optical module for endoscope comprising:

manufacturing an optical element, a first wafer, and a second wafer, the optical element including a light emitting section configured to output an optical signal or a light receiving section to which the optical signal is inputted, the optical element further including an external terminal connected to the light emitting section or the light receiving section, the first wafer including a first substrate including a first principal plane and a second principal plane opposed to the first principal plane the first substrate including, on the second principal plane, an annular seal ring and a connection electrode disposed on an inner side of the seal ring and electrically connecting with the seal ring, and the second wafer including a second substrate including a third principal plane and a fourth principal plane opposed to the third principal plane, the second substrate including an annular guard ring on the third principal plane, a lower electrode on the fourth principal plane, a through-wire electrically connecting the guard ring and the lower electrode, and a recessed section surrounded by the guard ring;

mounting the optical element on the second principal plane of the first substrate and bonding the external terminal of the optical element to the connection electrode of the first substrate;

bonding the seal ring of the first substrate and the guard ring of the second substrate via an annular solder ring to house the optical element in the recessed section of the second substrate, electrically connecting the external terminal to the lower electrode via the connection electrode, the seal ring, the solder ring, the guard ring, and the through-wire, and manufacturing a laminated wafer in which the recessed section is sealed up; and cutting and singulating the laminated wafer.

15. The manufacturing method for the optical module for endoscope according to claim 14, wherein the first wafer is made of a material substantially transparent with respect to light of the optical signal.

16. The manufacturing method for the optical module for endoscope according to claim 14, wherein the first wafer is made of silicon including a silicon oxide layer on the second principal plane, and a bottom surface of the insertion hole is configured by the silicon oxide layer.

17. The manufacturing method for the optical module for endoscope according to claim 14, further comprising inserting an optical fiber into an insertion hole of the first principal plane of the first substrate.

* * * * *